United States Patent [19]

Buttaravoli

[11] 4,324,237
[45] Apr. 13, 1982

[54] INTRAVENOUS CATHETER AND TUBING SECUREMENT AND DRESSING DEVICE WITH A WINDOW OVER THE PUNCTURE OR WOUND SITE

[75] Inventor: Philip M. Buttaravoli, Potomac, Md.

[73] Assignee: E-Med Corporation, Cincinnati, Ohio

[21] Appl. No.: 124,859

[22] Filed: Feb. 26, 1980

[51] Int. Cl.³ .............................................. A61M 5/00
[52] U.S. Cl. ................................................. 128/214 R
[58] Field of Search .... 128/214 R, DIG. 6, DIG. 16, 128/DIG. 28, 155, 156

[56] References Cited

U.S. PATENT DOCUMENTS

| | | | |
|---|---|---|---|
| 2,727,512 | 12/1955 | Muller | 128/DIG. 6 |
| 3,422,817 | 1/1969 | Mishkin et al. | 128/155 |
| 4,126,130 | 11/1978 | Cowden et al. | 128/156 |
| 4,192,304 | 3/1980 | Millet | 128/DIG. 16 |
| 4,221,215 | 9/1980 | Mandelbaum | 128/155 |
| 4,235,337 | 11/1980 | Dotta | 128/155 |

Primary Examiner—Gene Mancene
Assistant Examiner—Wenceslao J. Contreras
Attorney, Agent, or Firm—Frost & Jacobs

[57] ABSTRACT

A dressing device for securing on a body portion of a patient an infusion needle or catheter and a safety loop of the tubing associated therewith. The dressing device comprises a base strip of flexible material having an adhesive coating on its underside for attachment to the patient's skin and a gauze pad extending transversely of its central portion for direct contact with the puncture site. The base strip has a central longitudinal slit formed therein extending from an end edge of the base strip approximately to the middle thereof and terminating in a flap forming portion. That portion of the slit overlying the gauze pad, including the flap forming portion, extends through the gauze pad as well. The slit enables placement of the dressing device about the infusion needle or catheter with the flap forming portion located at the puncture site. A flexible cover strip has a first portion affixed to the upper surface of the base strip and a second portion covering the slit in the base strip. The second portion of the cover strip is releasably adherable to the upper surface of the base strip such that when the second portion of the cover strip is lifted from the base strip it will lift the flap formed in the base strip and the gauze pad exposing the puncture site. When adhered to the base strip, the second portion of the cover strip will close the flap formed on the base strip and gauze pad and will secure in place the infusion needle or catheter as well as a portion of its tubing formed into a safety loop. With simple modification, the dressing of the present invention can be used as a windowed dressing for a wound.

31 Claims, 17 Drawing Figures

INTRAVENOUS CATHETER AND TUBING SECUREMENT AND DRESSING DEVICE WITH A WINDOW OVER THE PUNCTURE OR WOUND SITE

TECHNICAL FIELD

The invention relates to a medical dressing having a reclosable window over the wound or puncture site and more particularly to such a dressing which, in one embodiment, can serve as a securement device for an intravenous catheter and its tubing and in another embodiment can serve as a dressing for a wound or the like.

BACKGROUND ART

While the teachings of the present invention are applicable to the provision of a windowed dressing for simple wounds, incisions or the like, as will be described hereinafter, they are particularly applicable to a securement dressing for an intravenous infusion needle or catheter and its tubing.

Intravenous feeding and transfusions are among the most frequently performed treatments in hospitals. Infusion apparatus employed in the intravenous feeding of blood, plasma, glucose water, salt water and the like comprises an infusion needle or catheter, a handle portion and a length of tubing connecting the needle to a source of intravenous fluid. Heretofore, the needle or catheter was inserted into the vein of the patient and constrained in position by small strips of adhesive tape attached to the handle portion of the infusion needle or catheter and to the skin of the patient so that the infusion needle or catheter could not be inadvertently dislodged. The puncture site of the needle or catheter was often protected with an antibacterial ointment and/or a gauze pad for the purpose of helping to lower the chance of infection. The gauze pad also served as a cushion if placed under the catheter and handle portion. The tubing, as well, was commonly secured to the skin of the patient with several strips of adhesive tape with a portion of the tubing coiled to form a loop and held in place by several additional strips of adhesive tape. The purpose of the coil or loop of the tubing was to absorb any unexpected tension placed on the tubing without disturbing the infusion needle or catheter.

More recently, prior art workers have developed devices intended to simplify and facilitate this rather complex cumbersome and time consuming procedure. Exemplary devices of this type are taught, for example, in U.S. Pat. Nos. 3,046,983; 3,136,158; 3,568,679; 3,782,378; 3,826,254; 3,834,380; 3,885,560; 3,918,446; 3,973,565; 4,059,105; 4,129,128 and U.S. Pat. Des. No. 243,715.

These prior art devices are, in general, characterized by one or more of the following deficiencies. Many of them are difficult to apply, and require removal of the protective layer or liners from their adhesive surfaces prior to placement about the puncture site. Many of them expose the puncture site directly to an adhesive surface. A number of them have no means for visual inspection of the puncture site, and sufficiently cover the area to hide evidence of phlebitis. Frequently, no absorbent means is provided to absorb blood at the puncture site or to absorb medicament for application to the puncture site. A number of the devices have no means for forming a safety loop in the tubing. Many do not provide cushioning of the infusion needle or catheter from the skin. Finally, it is a common requirement that the device be removed in order to change the tubing, inspect the puncture site, or to remove the infusion needle or catheter.

That embodiment of the present invention, comprising a securement device for an intravenous catheter and its tubing, is characterized by a very simple construction permitting easy placement, adjustment, and removal of the liners from the adhesive surfaces after placement about the puncture site. The device may be provided with a non-stick gauze pad which acts as a soft, absorbent cushion for the catheter or infusion needle. The gauze pad absorbs excess blood from the puncture site and the device does not subject the puncture site to adhesive. The gauze pad covers and surrounds the puncture site so that the device can be used as a pressure dressing after conclusion of the I.V. therapy to absorb blood after removal of the catheter or infusion needle. Furthermore, the gauze pad can absorb and retain medicaments at the puncture site.

The base portion of the dressing of the present invention has a longitudinal slit terminating in a flap-forming portion. This, in turn, is surmounted by a reclosable cover strip. This formation creates a flap in the base portion and gauze pad which lifts with the cover strip for direct visualization of the puncture site and/or application thereto of medicaments or the like. The slit also permits adjustment of the dressing so that the cover strip may or may not cover the catheter-tubing joint, as desired. The cover strip may also be used to anchor and retain a safety loop in the tubing. This safety loop can be arranged in one of two positions, a first position being such that the tubing can be changed without disturbing the puncture site, and the other position being such that the puncture site can be viewed without disturbing the tubing.

The dimensions of the dressing device are such that it can be located on the patient's hand without circumferentially wrapping thereabout, thus eliminating any possibility of a tourniquet effect. It is also sufficiently narrow that it will not cover evidence of phlebitis. Finally, the relatively thin gauze pad which is partially located beneath the infusion needle or catheter, allows the infusion needle or catheter to remain relatively parallel to the skin surface while serving as a cushion for it.

As indicated above, the teachings of the present invention are also applicable to a simple windowed dressing for a wound, incision or the like. Prior art workers have provided bandage devices having an access flap. Such a structure is taught, for example, in U.S. Pat. No. 1,610,089. The bandage structure, however, is of the wrap-around type and is not provided with a cover strip which lifts the access flap. Prior art workers have also devised bandage structures which are transparent so as to afford a view of the wound. Such structures are taught, for example, in U.S. Pat. Nos. 2,273,873 and 3,425,412.

DISCLOSURE OF THE INVENTION

According to the invention there is provided a dressing device having a reclosable window over the puncture site. In a first embodiment of the invention, the dressing device comprises means for securing on a body portion of a patient an infusion needle or catheter and its tubing. The dressing device comprises a base strip of flexible material having an adhesive coating on its underside for attachment to the patient's skin. A gauze pad may be affixed to its underside and extends transversely of the central portion of the base strip for direct contact with the puncture site. The base strip has a longitudinal slit formed therein which extends from one end edge of the base strip approximately to the middle of the base strip, terminating in a flap forming portion. That portion of the slit overlying the gauze pad extends through the gauze pad as well.

The dressing device also has a flexible cover strip substantially coextensive with the base strip. A first portion of the cover strip is affixed to the upper surface of the base strip and a second portion of the cover strip, covering the slit in the base strip, is releasably adherable to the upper surface of the base strip.

The structure is such that when the second portion of the cover strip is detached from and lifted from the base strip, it will lift the slap formed in the base strip and gauze pad by the aforementioned slit, exposing the puncture site. When adhered to the base strip, the second portion of the cover strip will close the flap formed in the base strip and gauze pad and will secure in place the infusion needle or catheter as well as a portion of its tubing formed into a safety loop. The adhesive coated underside of the base strip may be provided with a pair of removable liners in side-by-side relationship extending from the slit end of the base member to the center portion of the gauze pad and a third releasable liner extending from the other end of the base strip to the center portion of the gauze pad. The pair of liners and the third liner may meet edge-to-edge at the center of the gauze pad, or they may overlap. In similar fashion, the second portion of the cover strip, the underside of which is coated with a releasable adhesive, may be provided with a removable liner.

A second embodiment of the dressing device of the present invention may take the form of a simple dressing for a wound or incision. This embodiment is similar to the previously described first embodiment, differing only in that the base strip is not slit from an end edge to its central portion, but rather is provided simply with a flap-forming slit extending through the gauze pad as well. In this embodiment, a removable liner need not be provided for the second portion of the cover strip. Under these circumstances, the cover strip may be releasably adhered to the upper surface of the base strip from the outset, the cover strip being liftable from the base strip, lifting the flap formed in the base strip and the gause pad with it.

In a third embodiment of the present invention, a simple windowed bandage or dressing is provided, in this embodiment, the base strip has a fully cut out aperture formed therein. The releasable cover strip may have a gauze pad mounted therein in such position as to enter and be coextensive with the aperture in the base strip when the cover strip is in its closed position.

BEST MODE OF CARRYING OUT THE INVENTION

Figure 1:
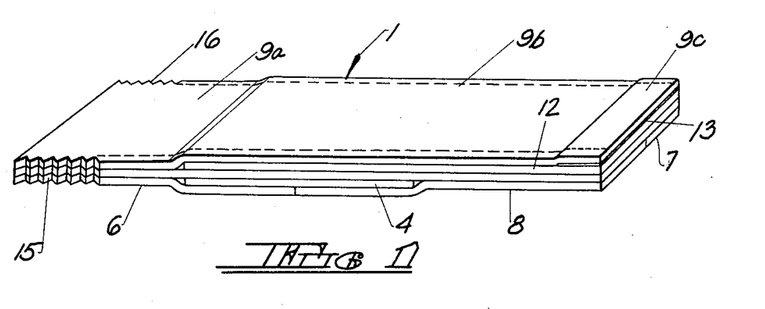
FIG. 1 is a perspective view of a first embodiment of the dressing device of the present invention.
Figure 2:
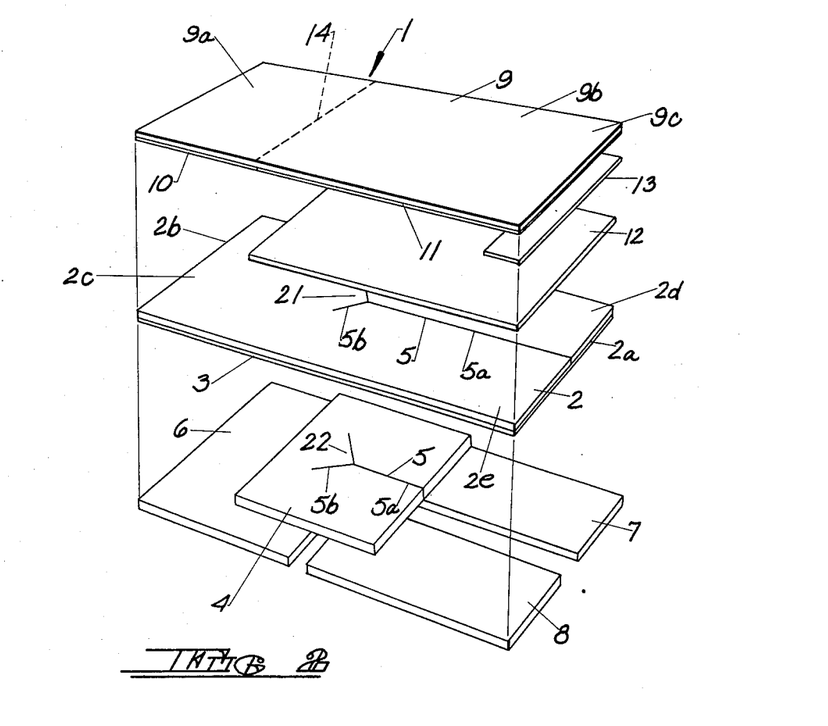
FIG. 2 is an exploded perspective view of the dressing device of FIG. 1.
Figure 3:
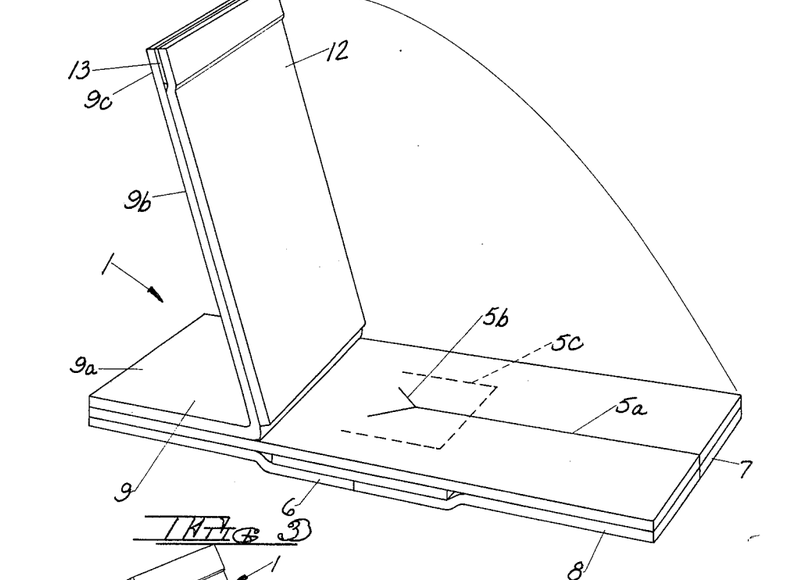
FIG. 3 is a perspective view of the dressing device of FIGS. 1 and 2 with its cover strip in its open position.

Reference is first made to FIGS. 1 through 3 wherein a first embodiment of the present invention is illustrated and wherein like parts have been given like index numerals. Throughout the drawings the various plies or layers of cloth tape, gauze and liner material have been exaggerated in thickness for purposes of clarity. FIG. 1 illustrates the embodiment ready for use. FIG. 2 is an exploded view of the embodiment and FIG. 3 is similar to FIG. 1 with the cover strip pulled away from and lifted from the base strip.

The embodiment of FIGS. 1 through 3 is in the form of an intravenous catheter and tubing securement and dressing device, which device is generally indicated at 1. The dressing device comprises a base strip 2 which may be made of any appropriate material for use in a medical environment. Preferably, the base strip 2 is made of a cloth tape having on its underside a coating of adhesive 3 suitable for adhering the base strip 2 to the patient's skin. Such cloth tape and adhesive are widely known in the art for their hypoallergenic and adhesive qualities. Affixed to the bottom surface of base strip 2 there may be a gauze pad 4 which is located centrally of the base strip and extends transversely thereof. The gauze pad 4 may again be made of any appropriate and well known material suitable for a medical environment. Preferably, the gauze pad 4 comprises medical grade non-stick gauze. Gauze pad 4 will be permanently affixed to the underside of base strip 2 by virtue of the adhesive layer 3 on the base strip. The assembly of the base strip 2 and gauze pad 4 has a slit 5 formed therein. The slit 5 comprises a first rectilinear portion 5a which extends from the end edge 2a of base strip 2 along the longitudinal centerline of the base strip to about the center of the base strip. The slit 5 has a second portion 5b which is a flap forming portion. In the embodiment shown, the flap forming portion 5b is V-shaped so that the overall slit 5 is generally Y-shaped. It will be understood by one skilled in the art that the flap forming portion 5b of slit 5 can have any appropriate configuration including (but not limited to) a U-shaped configuration, a semi-circular configuration, or the like. In similar fashion, the size of the flap forming portion 5b of slit 5 can vary. To indicate this, an alternate enlarged U-shaped flap forming portion 5c is indicated in broken lines in FIG. 3.

As a result of slit 5, base strip 2 may be considered as having three portions. Thus, from end edge 2b up to the flap forming slit portion 5a may be considered to be a body portion 2c and the remainder of base strip 2 is formed into legs 2d and 2e by slit 5. To complete the base structure, conventional, removable liners may be provided to protect the adhesive coated surfaces of base strip 2 and the bottom surface of gauze pad 4. One such liner 6 covers approximately half of the underside of gauze pad 4 and the underside of the body portion 2c of base strip 2. Additional liners 7 and 8 are provided to cover the remainder of the underside of gauze pad 4 and the undersides of leg portions 2d and 2e, respectively, of base strip 2. In the embodiment illustrated, the liner 6 and the liners 7 and 8 are shown as meeting beneath gauze pad 4. It would be within the scope of the invention to cause liner 6 to overlap the adjacent edge portions of liners 7 and 8, or vice versa, beneath gauze pad 4. Liners 6, 7 and 8 may be made of identical material appropriate and well known for such purposes such as paper, plastic or the like, readily releasable from the adhesive layer 3 on the underside of base strip 2.

A cover strip is shown at 9. The cover strip 9 may be made of the same material as base strip 2. Cover strip 9 is illustrated as being of the same dimensions and coextensive with base strip 2. The cover strip 9 need not be of the same dimensions or shape as base strip 2 so long as it is of sufficient size to perform its functions described hereinafter. The cover strip 9 has a first portion 9a affixed to the upper surface of body portion 2c of base strip 2 by any appropriate adhesive layer 10 on the underside of cover strip portion 9a or by other suitable connective means. As can be most easily determined from FIGS. 1 and 3, the portion 9a of cover strip 9 constitutes approximately ⅓ of the cover strip.

The remainder of the cover strip constitutes a second portion 9b provided on its underside with a layer 11 of releasable and resealable adhesive, as is well known in the art. The adhesive layer 11 is protected by a removable liner 12 similar to liners 6, 7 and 8. In FIGS. 2, adhesive layers 3, 10 and 11 are illustrated as separate visible layers, for purposes of an exemplary showing, it will be understood that these are coatings of adhesive on the undersides of base strip 2 and cover strip 9 and would not, in reality, appear as separate layers having a noticable thickness dimension.

It is preferable to have the endmost part 9c of the free end of second portion 9b of cover strip 9 constitute a tab which is not adhered to liner 12 and can readily be lifted from liner 12 so that the liner 12, in turn, can be easily removed from the underside of second portion 9b of cover strip 9. This can be accomplished in several ways. First of all, an additional narrow liner 13 may be permanently adhered to the endmost portion 9c of cover strip 9. Alternatively, the adhesive layer 11 may stop short of the endmost portion 9c. The endmost portion 9c of cover strip 9 also serves as a tab for lifting cover strip portion 9b from base strip 2 when adhered thereto in use.

Various modifications can be made in the embodiment of FIGS. 1 through 3, which modifications fall within the scope of the present invention. For example, in FIGS. 1 through 3 gauze pad 4 is shown extending the full width of base strip 2. The gauze pad 4 may have a width dimension less than base strip 2 so that the adhesive layer or coating 3 will contact the patient's skin on all sides of gauze pad 4. Similarly, while adhesive layers or coatings 10 and 11 are preferably applied to the underside of cover strip 9, they could be applied to the upper surface of base strip 2. In such an instance, liner 12 would be affixed to the upper surface of base strip 2, rather than the under surface of cover strip 9. The adhesive coating 10 or other means affixing cover strip portion 9a to base strip 2 may be such as to make this attachment permanent, more difficultly releasable than the portion 9b or as releasable and resealable as portion 9b. For most uses it is preferable that this attachment be permanent or more difficultly releasable. Furthermore, it will be understood that the juncture of portions 9a and 9b of cover strip 9 constitute a hinge line which is indicated by a broken line 14 in FIG. 2. It would be possible to fold liner 12 in such a way as to have a portion (not shown) folded back upon itself for about ⅛" or so, adjacent hinge line 14, to serve as a removal tab for liner 12.

Finally, it is preferable that the longitudinal edges of base strip 2 and cover strip 9 be serrated when these strips are made of cloth tape to prevent unraveling. Where the structure of FIGS. 1 through 3 is assembled as a continuous structure cut transversely to form the individual dressing devices, these cuts could be made with a serrated cutting means with the result that the longitudinal corresponding edges of cover strip 9, liner 13, liner 12, base strip 2, gauze pad 4 and liners 6, 7 and 8 would all be serrated. Such serrated edges are diagrammatically indicated at 15 and 16 in FIG. 1.

Figures 4, 5:
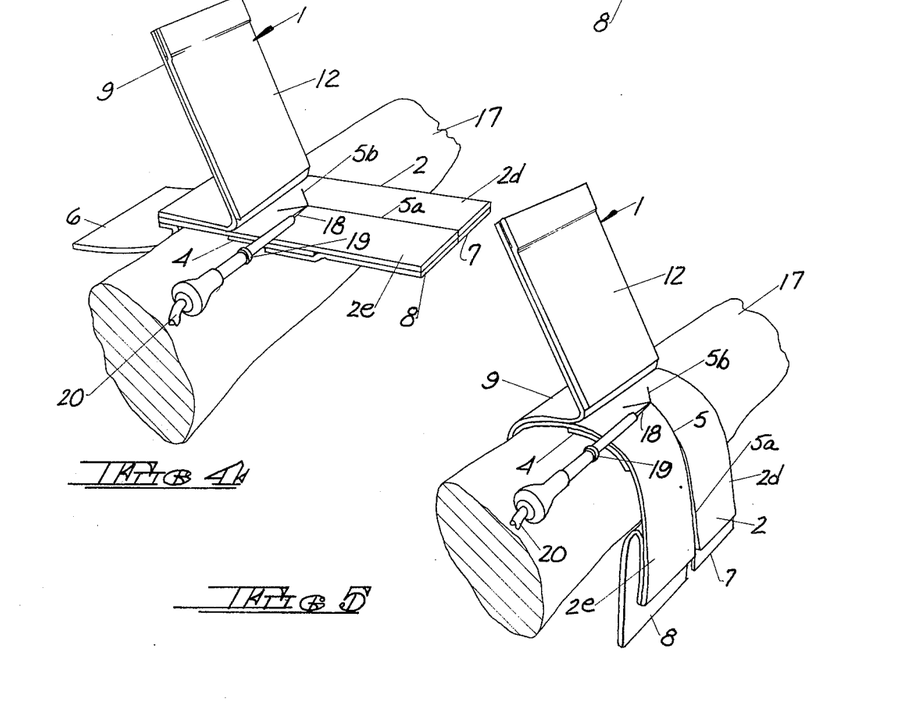
FIGS. 4 through 9 are perspective views illustrating the placement and use of the embodiment of FIGS. 1 through 3 on a body portion of a patient.

FIGS. 4 through 9 are intended to sequentially illustrate the application and use of the embodiment of FIGS. 1 through 3. Again, like parts have been given like index numerals. Reference is first made to FIG. 4. In FIG. 4 a patient's arm is indicated at 17. A catheter or infusion needle 18 is shown, together with its connection 19 to a tubing member 20 which, in turn, is connected to a source of I.V. fluid (not shown). Once the infusion needle or catheter 18 is properly located in the patient's arm 17, the dressing device 1 can be located about the infusion needle or catheter. This is done by shifting the cover strip 9 to its open position and locating the leg portions 2a and 2b of base strip 2 to either side of the needle. The configuration of slit 5 is such that the legs 2a and 2b can be spread apart with leg 2b located beneath the infusion needle or catheter 18 without the necessity of sliding the dressing device along the needle during placement. The bandage can be positioned in such a way that the infusion needle or catheter 18 is so located with respect to the flap forming portion 5b of slit 5 that the connection 19 between infusion needle or catheter 18 and tubing 20 will or will not be covered by cover strip 9, as desired. When the dressing device is properly located as shown in FIG. 4, the liner 6 may be removed from the body portion 2c of base strip 2 and the body portion 2c of the base strip can be pressed to the skin for adhesive attachment thereto. Since the liner 6 partially overlaps gauze pad 4, that portion overlapping the gauze pad 4 will automatically serve as a removal tab for the liner 6.

Figure 6:
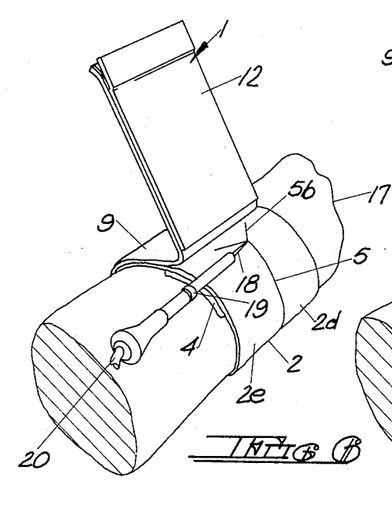
Figure 7:
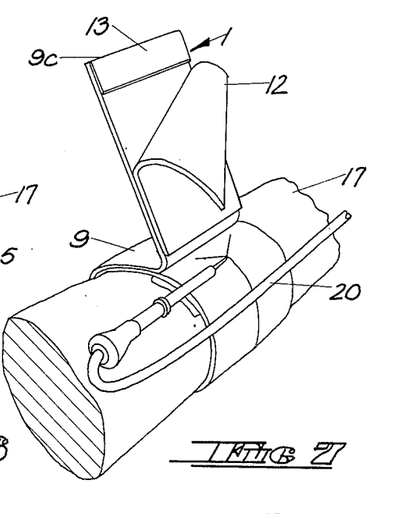
Figure 8:
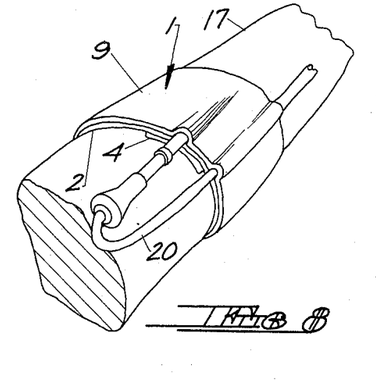

Thereafter, the liners 7 and 8 may be removed from leg portions 2d and 2e of base strip 2 and leg portions 2d and 2e can then be adhesively affixed to the patient's arm 17, as shown in FIG. 6. At this point, the safety loop formed in tubing 20 is laid along the upper surface of leg portion 2d and 2e of base strip 2 as shown in FIG. 6. The liner 12 is then removed from cover strip 9, as shown in FIG. 7. As a final step, the cover strip 9 is adhered to the upper surface of base strip 2, covering the catheter or infusion needle 18 and the tubing 20, as shown in FIG. 8. It will be noted from FIG. 8 that the juncture 19 of infusion needle or catheter 18 and tubing 20 has been so located with respect to the flap forming portion 5b of slit 5 that the juncture is uncovered by cover strip 9. It will also be evident from FIG. 8 that tubing 20 is firmly engaged by cover strip 9. At this point, the procedure for inserting and securing the catheter or infusion needle 18 and its tubing 20 is complete.

If it is subsequently desired to inspect the puncture site or to apply medicament thereto, it is only necessary to lift cover flap 9 from base strip 2. This is made easy by tab portion 9c of the cover flap.

Figure 9:
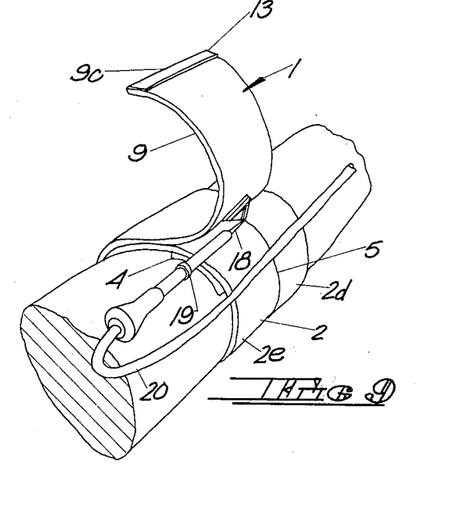

Returning to FIG. 2, it will be evident that the flap forming portion 5b of slit 5 forms a V-shaped flap 21 in cover strip 2 and a similar V-shaped flap 22 in gauze pad 4. Since the underside of base strip 2 is provided with adhesive coating 3, the gauze pad flap 22 will be adhered to the base strip flap 21. Base strip flap 21, in turn, is adhered to the underside of cover strip 9 by virtue of releasable adhesive coating 11. Since the flap 22 of gauge pad 4 is not adhered to the skin, when cover flap 9 is raised as shown in FIG. 9 the base strip flap 21 and attached gauze pad flap 22 will lift with it. In this way, the puncture site is exposed for inspection and/or the application of medicament. Upon readhering cover strip 9 to the upper surface of base strip 2, flaps 21 and 22 will reclose and be held in closed position.

It will be further evident from FIG. 8 that if the infusion needle or catheter 18 is so located with respect to flap forming slit portion 5a that its connection 19 with tubing 20 is not covered by cover strip 9 when in its closed position, it would be possible to change tubing 20 by lifting cover strip 9 sufficiently to release the tubing, without disturbing or lifting flaps 21 and 22 at the puncture site.

Figure 10:
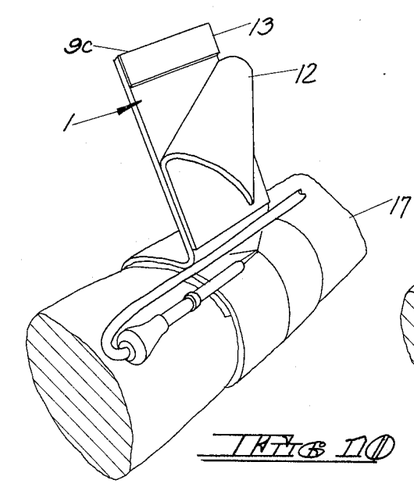
FIGS. 10 through 12 are perspective views, similar to FIGS. 7 through 9, respectively, and illustrating an alternate positioning of the catheter or infusion needle tubing.
Figure 11:
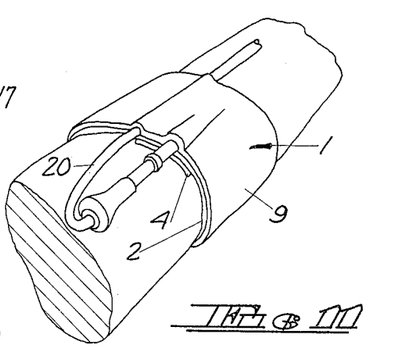

FIG. 10 is similar to FIG. 7 and like parts have been given like index numerals. FIG. 10 differs from FIG. 7 only in that it shows an alternate positioning of tubing 20. In this instance the tubing 20 is formed into a loop and is placed on the upper surface of base strip 2 behind the flap forming slit portion 5a near the hinge line of cover strip 9. When cover strip 9 is closed, as shown in FIG. 11, the assembly is the same as that shown in FIG. 8 with the exception that the portion of tubing 20 secured by cover strip 9 is located to the other side of catheter or infusion needle 18. Under these circumstances, cover strip 9 can be lifted together with flaps 21 and 22 without disturbing tubing 20. Upon completion of inspection of the puncture site and/or application of medicament thereto, the cover strip can be reclosed and the tubing 20 will have been firmly held in place throughout the inspection process. To increase securement of tubing 20 even more, the tubing may be looped a second time so that it can be held in place twice by cover strip portion 9b. This is shown in broken lines at 20a in FIG. 12.

From FIGS. 4 through 12, it will be evident that the dressing device 1 is sufficiently narrow that that end of infusion needle or catheter 18 located beneath the skin will be near or beyond the edge of the dressing device 1 so that a phlebitic condition can readily be visually detected and will not be masked or covered by the dressing device 1.

Figures 12, 13:
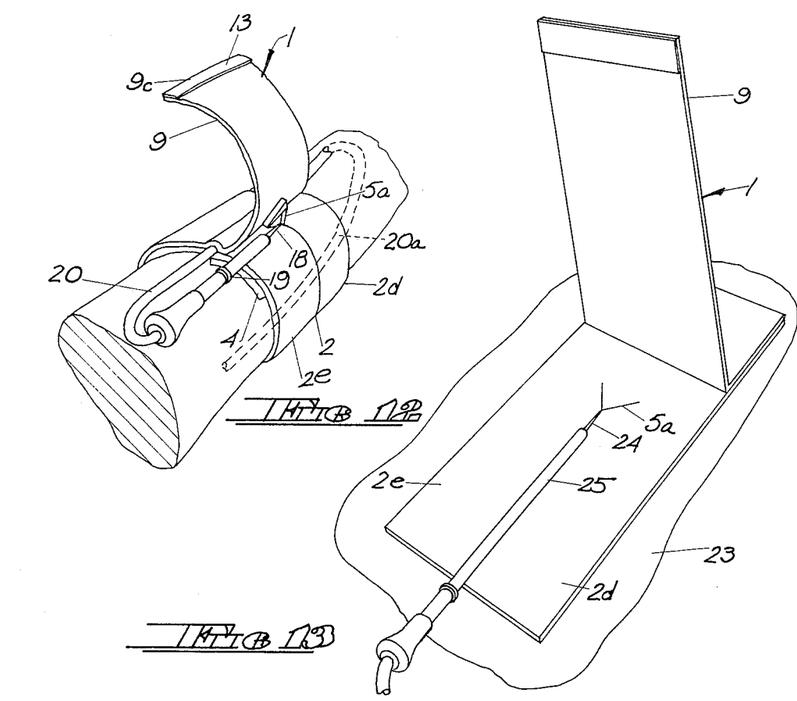
FIG. 13 is a perspective view illustrating an alternate mounting of the dressing device of FIGS. 1 through 3 on a body portion of a patient.

In the case of a subclavian I.V. treatment, the catheter or infusion needle is provided with an extremely long hub portion. In such an instance, the dressing device 1 of the present invention can be used to advantage by having its long axis extend in the direction of the infusion needle or catheter. This is illustrated in FIG. 13. In this Figure a portion of the patient's body is shown at 23 and an infusion needle or catheter is shown at 24 having an elongated hub 25. The bandage device 1 is applied in the same manner described with respect to FIGS. 4 through 9 with the exception that the long axis of the dressing device 1 is oriented parallel to the axis of catheter or infusion needle 24. The needle 24 and its elongated hub 25 will be firmly held in place when the cover strip 9 is located in its closed position. In such an instance there would be no safety loop in the tubing (not shown).

Figure 14:
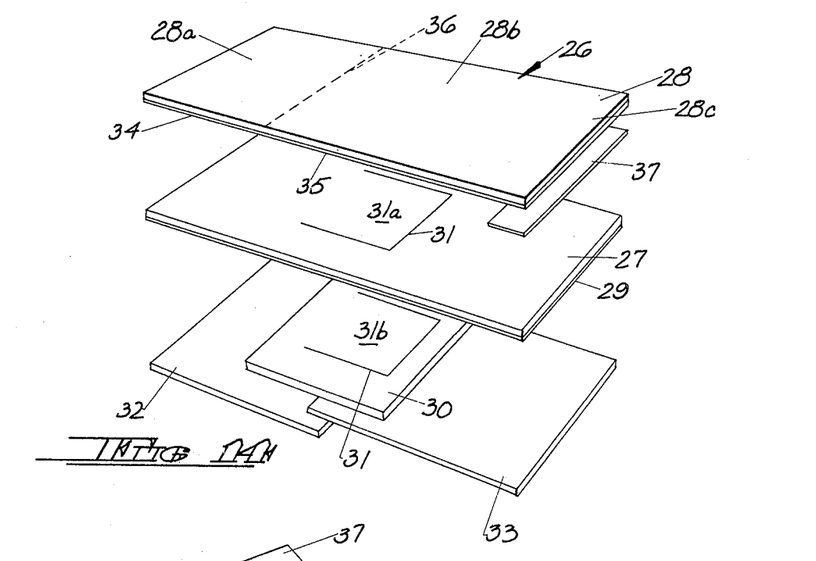
FIG. 14 is an exploded, perspective view of a second embodiment of the dressing device of the present invention.
Figure 15:
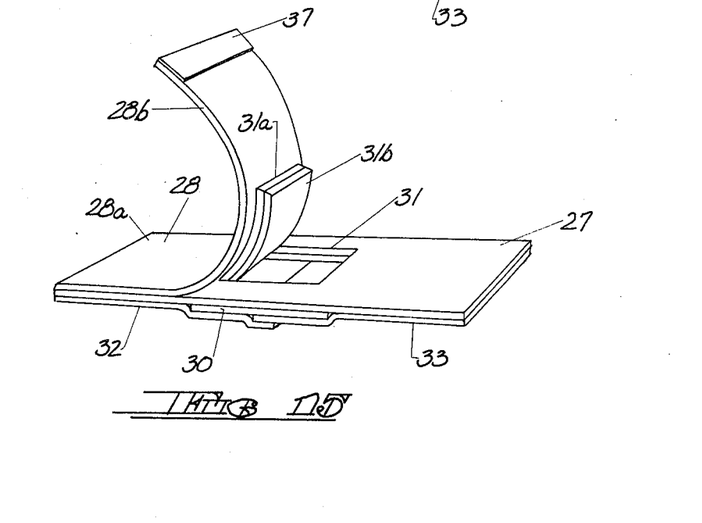
FIG. 15 is a perspective view of the dressing device of FIG. 14 with its cover strip in open position.

Reference is now made to FIGS. 14 and 15 illustrating a second embodiment of the dressing device of the present invention adapted to serve as a dressing for a wound or incision. Again, like parts are given like index numerals. FIG. 14 is an exploded view of the dressing device, generally indicated at 26. The dressing device comprises a base strip 27 and a cover strip 28 which may be substantially identical to and which may be made of the same materials described with respect to base strip 2 and cover strip 9 of FIG. 2. The underside of base strip 27 is provided with an adhesive coating (shown for purposes of clarity in FIG. 14 as a layer 29). A gauze pad 30, similar to gauze pad 40 of FIG. 2, may be affixed to the underside of base strip 27. The base strip 27 and gauze pad 30 differ from base strip 2 and gauze pad 4 of FIG. 2 in that they are not provided with a longitudinally extending slit from an end edge such as slit portion 5a in FIG. 2. Rather, base strip 27 and gauze pad 30 are provided simply with a flap forming slit 31 extending through both of these elements. As in the case of flap forming slit portion 5b of FIG. 2, slit 31 may take any appropriate configuration including U-shaped, V-shaped, semi-circular or the like. As is true of flap forming slit portion 5b of FIG. 2, the flap forming slit 31 can be varied in size and, since the dressing device 21 is intended for use with a wound or incision, the flap-forming slit 31 will preferably be somewhat larger with respect to the overall dressing device 26 than is flap forming slit portion 5b of FIG. 2 with respect to dressing device 1.

Gauze pad 31 may have the same transverse width as base strip 27, as shown in FIGS. 14 and 15, or it may be slightly narrower so that the base strip 27 is adhesively affixed to the patient's skin completely about gauze pad 30.

The assembly of base strip 27 and gauze pad 30 is provided with a pair of liners 32 and 33. Liner 32 is equivalent to liner 6 of FIG. 2, while liner 33 is equivalent to both liners 7 and 8 of FIG. 2. As mentioned above with respect to liners 6, 7 and 8, liners 32 and 33 can meet beneath gauze pad 30, or they can be slightly overlapped as shown in FIGS. 14 and 15.

Cover strip 28 is identical to cover strip 9 of FIG. 2. Cover strip 28 has a first portion 28a affixed to the upper surface of base strip 27 by adhesive layer 34 on the underside of portion 28a, or by other means. Once again, portion 28a is preferably permanently affixed to base strip 27, but it may also be releasably affixed, if desired. The first portion 28a of cover strip 28 constitutes about ⅓ of the cover strip. A second portion 28b of cover strip 28 is provided on its underside with a coating 35 of releasable and resealable adhesive, by which the portion 28b can be removably adhered to the upper surface of base strip 27. The juncture of portions 28a and 28b constitutes a hinge line for cover strip 28, this hinge line being shown in broken lines at 36.

The endmost part 28c of the free end of cover strip portion 28b preferably serves as a tab by which cover strip 28 can be grasped so as to be pulled up from base strip 27. This can be accomplished in the same ways described with respect to FIG. 2. Thus, adhesive coating 25 may terminate short of the free end of cover strip portion 28b so that the tab portion 28c is free of releasable adhesive 35. Alternatively, the tab portion 28c may have a liner 37 affixed thereto so that it will not stick to the upper surface of base strip 27.

From the above description it will be evident that the embodiment of FIGS. 14 and 15 differs from the embodiment of FIGS. 1 through 3 primarily in that only two liner members 32 and 33 need be provided for base strip 27. The base strip 27 and gauze pad 31 have only a flap-forming slit 31 formed therein. Finally, a liner for cover strip 28 equivalent to liner 12 of FIG. 2 is not required. In the embodiment of FIGS. 14 and 15, the cover flap portion 28b will be adhered to the upper surface of base strip 27 unless lifted for purposes of inspecting the wound or incision site.

To apply the dressing device 26 of FIGS. 14 and 15, it is only necessary to remove liners 32 and 33 from base strip 27. This can readily be accomplished since those portions of liners 32 and 33 extending over gauze pad 31 will not be adhered to the gauze pad and will readily serve as removal tabs. The slit 31 in base strip 27 and gauze pad 30 forms flaps 31a in base pad 27 and 31b in gauze pad 31. The dressing device 26 will be so located with respect to the wound or incision that flaps 31a and 31b will be positioned thereover. The dressing device 36 is then pressed against the skin of the patient for attachment thereto by adhesive layer 29.

When it is desired to inspect the wound or incision, or to apply medicament thereto, it is only necessary to lift cover strip portion 28b. Since gauze pad flap 31b is adhered to base strip flap 31a and base strip flap 31a is adhered to cover strip portion 28b, a lifting of cover strip portion 28b will cause a lifting of flaps 31a and 31b as well. Reclosing of cover strip portion 28b will result in a reclosing of flaps 31a and 31b. When base strip 27 and cover strip 28 are made of a cloth tape, it is again preferable that their longitudinal edges be serrated as shown and described with respect to FIG. 1. Adhesive coatings 34 and 35 could be applied to the upper surface of base strip 27, rather than on the lower surface of cover strip 28. Under these circumstances, liner 37 would be affixed to upper surface of base strip 27.

Figure 16:
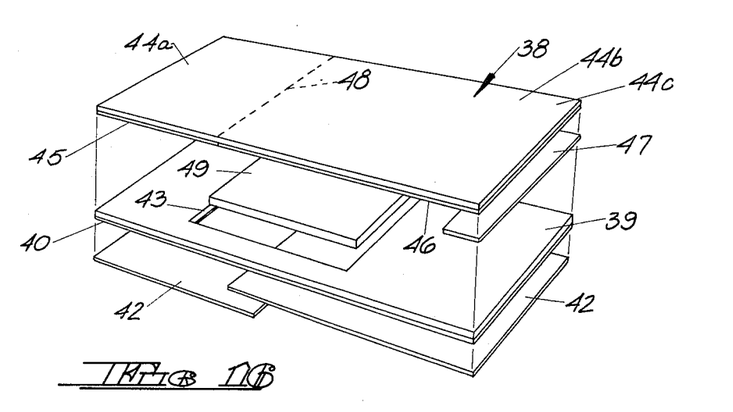
FIG. 16 is an exploded, perspective view of a third embodiment of the dressing device of the present invention.
Figure 17:
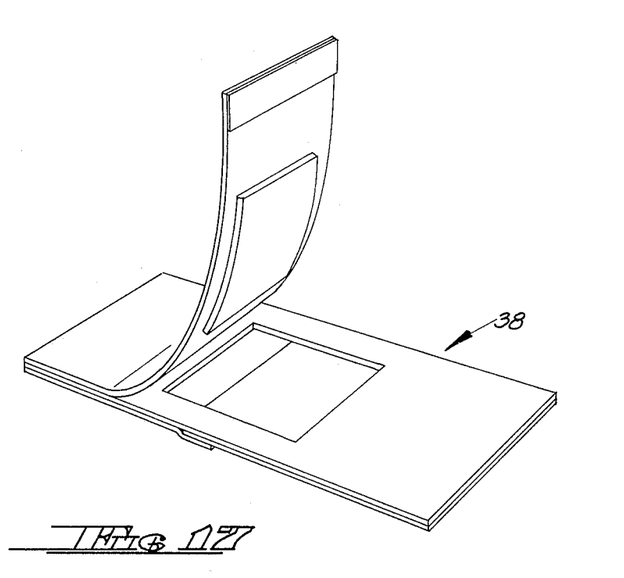
FIG. 17 is a perspective view of the dressing device of FIG. 16 with its cover strip in open position.

Reference is now made to FIGS. 16 and 17 illustrating a third embodiment of the dressing device of the present invention. The embodiment of FIGS. 16 and 17 constitutes a modification of FIGS. 14 and 15. Like index numerals are used in FIGS. 16 and 17 and the dressing device shown therein is generally indicated at 38. In this embodiment, a base strip 39 is provided, having an adhesive coating 40 on its underside equivalent to adhesive coating 29 of FIG. 14. The adhesive coating 40 is of the type adapted to affix base strip 39 to the skin of the patient. The adhesive coating 40 is protected by a pair of liners 41 and 42. Liners 41 and 42 may meet at the center of base strip 39 or be slightly lapped, as shown. Base strip 39 differs from base strip 27 of FIG. 14 only in that instead of being provided with a flap-forming slit equivalent to slit 31, base strip 39 is provided with a complete cut-out forming a window 43.

The dressing device 38 is also provided with a cover strip 44 substantially identical to cover strip 28 of FIG. 14. Cover strip 44 has a first portion 44a provided with an adhesive layer 45 on its underside by which the portion 44a may be permanently or resealably affixed to the upper surface of base strip 39. Cover strip 44 has a second portion 44b provided on its underside with a layer of releasable and resealable adhesive 46 and a tab portion 44c which is either devoid of adhesive 46 or is provided with a liner 47 equivalent to liner 37 of FIG. 14. The juncture of portions 44a and 44b of cover strip 44 constitutes a hinge line shown in broken lines at 48.

A gauze pad 49 similar to gauze pad 30 of FIG. 14 may be provided. In this instance, the gauze pad 49 (again preferably comprising medical grade non-stick gauze) is affixed directly to the portion 44b of cover strip 44. The gauze pad 49 may be of the same width as cover strip 44 and base strip 39, as shown, or it may be the same size as window 43. In the former instance, it will be positioned on cover strip portion 44b as to cover window 43 when the cover strip portion is in its closed position. In the latter instance, it will be so positioned with respect to cover strip portion 44b as to be coextensive with and located in window 43 when the cover strip is in its closed position.

The dressing device 38 of FIGS. 16 and 17 is applied to the patient in the same manner described with respect to dressing device 26 of FIGS. 14 and 15. When it is desired to inspect the wound or incision of the patient or to apply medicament thereto, it is only necessary to lift cover strip 44. When this is done, gauze pad 49 will lift with the cover strip exposing the wound or incision through window 43. Upon reclosure of the cover flap, gauze pad 49 will again be located and secured over the wound or incision. The embodiment of FIGS. 16 and 17 differs from that of FIGS. 14 and 15 only in the placement of guaze pad 49 and the provision of window 43 rather than a flap-forming slit 31 in base strip 39. Once again, if base strip 39 and cover strip 44 are made of cloth tape, the longitudinal edges of these elements are preferably serrated.

Modifications may be made in the invention without departing from the spirit of it. For example, all of the embodiments can be made in various sizes, proportions and shapes, depending upon their ultimate use. In all of the embodiments, the cover strip need not be the same size or shape as the base strip. In the embodiment of FIGS. 1 through 13, the slit 5 could extend inwardly from any appropriate edge portion and there could be more than one slit 5. The flap forming portion of slit 5 could be eliminated. Finally, in all of the embodiments the guaze pad could be eliminated.

What is claimed is:

1. A dressing device to cover a desired site on the skin of a patient, said dressing device comprising a base strip having upper and lower surfaces, an adhesive coating on said lower surface of said base strip to attach said base strip to said skin of the patient adjacent said site, access means in said base strip to said site, an elongated cover strip having upper and lower surfaces, a first portion of said cover strip being affixed to said upper surface of said base strip spaced from said access means, a second portion of said cover strip being releasably and resealably affixable to said base strip upper surface by releasable and resealable adhesive applied to one of said lower surface of said cover strip and said upper surface of said base strip, said cover strip being shiftable between a closed position adhered to said upper surface of said base strip and covering said access means in said base strip and an open position exposing said access means, and a gauze pad affixed to the underside of one of said base strip and said cover strip so as to contact said site when said cover strip is in said closed position and to expose said site when said cover strip is in said open position.

2. The structure claimed in claim 1 wherein said base strip and said cover strip are made of medical grade cloth tape and said gauze pad comprises a medical grade non-stick gauze pad.

3. The structure claimed in claim 1 including at least one removable liner protecting said adhesive coating on said lower surface of said base strip.

4. The structure claimed in claim 1 wherein said dressing device comprises an intravenous catheter and tubing securement, said base strip comprising an elongated member having first and second ends, said gauze pad being affixed to the lower surface of said base strip at the longitudinal center thereof by said adhesive coating thereon, said base strip having a slit formed therein, said slit having a first rectalinear portion extending inwardly from an edge of said base strip and terminating in a second flap forming portion, a part of said first slit portion and all of said second flap forming portion of said slit overlying and extending through said gauze pad, a flap formed in said base strip and a flap formed in said gauze pad by said flap forming second portion of said slit, said gauze pad flap being attached to said base strip flap by said adhesive on said lower surface of said base strip to form a flap assembly, said flap assembly comprising said access means to said site, said site comprising the puncture site of said catheter, said flap assembly being attachable to said second portion of said cover strip by said releasable and resealable adhesive, said flap assembly being shiftable by said cover strip second portion between an open position exposing said site and closed position covering said site.

5. The structure claimed in claim 1 wherein said dressing device comprises a dressing for a wound, incision and the like, said gauze pad being affixed to the lower surface of said base strip at the longitudinal center thereof by said adhesive coating thereon, said base strip and said guaze pad having a slit therein forming coextensive flaps therein, said gauze pad flap being attached to said base strip flap by said adhesive on said lower surface of said base strip to form a flap assembly, said flap assembly comprising said access means to said site, said site comprising said wound, incision and the like, said flap assembly being attached to said second portion of said cover strip by said releasable and resealable adhesive, said flap assembly being shiftable between an open position exposing said site and a closed position covering said site by said cover strip second portion.

6. The structure claimed in claim 1 wherein said dressing device comprises a dressing for a wound, incision and the like, said base strip having an aperture therein at the longitudinal center thereof, said aperture comprising said access means to said site, said site comprising said wound, incision and the like, said gauze pad being affixed to the lower surface of said cover strip second portion and shiftable thereby between an open position exposing said site when said cover strip second portion is in said open position and a closed position covering said site when said cover strip second portion is in said closed position.

7. The structure claimed in claim 4 wherein said base strip and said cover strip are made of medical grade cloth tape and said gauze pad comprises a medical grade non-stick gauze pad.

8. The structure claimed in claim 4 wherein said flap forming portion of said slit is V-shaped, said slit being Y-shaped.

9. The structure claimed in claim 4 including first and second removable liners to protect said adhesive coating on said lower surface of said base strip to either side of slit, a third removable liner to protect the remainder of said adhesive coating on lower surface of said base strip, said first, second and third removable liners covering the underside of said gauze pad, and a fourth removable liner to protect said releasable and resealable adhesive coating on one of said lower surface of said second cover strip portion and said upper surface of said base strip.

10. The structure claimed in claim 4 wherein said gauze pad is of the same width as said base strip.

11. The structure claimed in claim 4 wherein said gauze pad is of lesser width than said base strip.

12. The structure claimed in claim 4 wherein said first portion of said cover strip is permanently affixed to said upper surface of said base strip.

13. The structure claimed in claim 4 wherein said first portion of said cover strip is releasably affixed to said upper surface of said base strip.

14. The structure claimed in claim 5 wherein said base strip and said cover strip are made of medical grade cloth tape and said gauze pad comprises a medical grade non-stick gauze pad.

15. The structure claimed in claim 5 including two removable liners protecting said adhesive coating on said lower surface of said base strip, said liners meeting beneath and protecting said gauze pad.

16. The structure claimed in claim 5 wherein said gauze pad is of the same width as said base strip.

17. The structure claimed in claim 5 wherein said gauze pad is of lesser width than said base strip.

18. The structure claimed in claim 5 wherein said first portion of said cover strip is permanently affixed to said upper surface of said base strip.

19. The structure claimed in claim 5 wherein said first portion of said cover strip is releasably affixed to said upper surface of said base strip.

20. The structure claimed in claim 6 wherein said base strip and said cover strip are made of medical grade cloth tape and said gauze pad comprises a medical grade non-stick gauze pad.

21. The structure claimed in claim 6 including two removable liners protecting said adhesive coating on said lower surface of said base strip, said liners meeting beneath said aperture and protecting said gauze pad exposed thereby.

22. The structure claimed in claim 6 wherein said gauze pad is of the same width as said base strip.

23. The structure claimed in claim 6 wherein said gauze pad is the same dimensions as said aperture.

24. The structure claimed in claim 6 wherein said first portion of said cover strip is permanently affixed to said upper surface of said base strip.

25. The structure claimed in claim 6 wherein said first portion of said cover strip is releasably affixed to said upper surface of said base strip.

26. A dressing device to cover a desired site on the skin of a patient, said dressing device comprising a base strip having upper and lower surfaces, an adhesive coating on said lower surface of said base strip to attach said base strip to said skin of the patient adjacent said site, access means in said base strip to said site, an elongated cover strip having upper and lower surfaces, a first portion of said cover strip being affixed to said upper surface of said base strip spaced from said access means, a second portion of said cover strip being releasably and resealably affixable to said base strip upper surface by releasable and resealable adhesive applied to one of said lower surface of said cover strip and said upper surface of said base strip, said cover strip being shiftable between a closed position adhered to said upper surface of said base strip and covering said access means in said base strip and an open position exposing said access means, and a gauze pad affixed to the underside of said base strip so as to contact said site.

27. The structure claimed in claim 26 wherein said dressing device comprises an intravenous catheter and tubing securement, said base strip comprising an elongated member having first and second ends, said gauze pad being affixed to the lower surface of said base strip at the longitudinal center thereof by said adhesive coating thereon, said base strip having a slit formed therein, said slit being rectalinear and extending inwardly from an edge of said base strip and terminating at about the longitudinal center of said base strip, a part of said slit overlying and extending through said gauze pad, said said slit comprising said access means to said site, said site comprising the puncture site of said catheter, said cover strip being shiftable between an open position exposing said slit and a closed position covering said slit.

28. A dressing device to cover a desired site on the skin of a patient, said dressing device comprising a base strip having upper and lower surfaces, an adhesive coating on the lower surface of said base strip to attach said base strip to said skin of the patient adjacent said site, access means in said base strip to said site, an elongated cover strip having upper and lower surfaces, a first portion of said cover strip being affixed to said upper surface of said base strip spaced from said access means, a second portion of said cover strip being releasably and resealably affixable to said base strip upper surface by releasable and resealable adhesive applied to one of said lower surface of said cover strip and said upper surface of said base strip, said cover strip being shiftable between a closed position adhered to said upper surface of said base strip and covering said access means in said base strip and an open position exposing said access means in said base strip.

29. The structure claimed in claim 28 wherein said dressing device comprises an intravenous catheter and tubing securement, said base strip comprising an elongated member having first and second ends, said base strip having a slit formed therein, said slit having a first rectilinear portion extending inwardly from an edge of said base strip and terminating in a second flap forming portion, a flap formed in said base strip by said flap forming second portion of said slit, said flap comprising said access means to said site, said site comprising the puncture site of said catheter, said flap being attachable to said second portion of said cover strip by said releasable and resealable adhesive, said flap being shiftable by said cover strip second portion between an open position exposing said site and a closed position covering said site.

30. The structure claimed in claim 28 wherein said dressing device comprises a dressing for a wound, incision and the like, said base strip having a slit therein forming a flap therein, said flap comprising said access means to said site, said site comprising said wound, incision and the like, said flap being attached to said second portion of said cover strip by said releasable and resealable adhesive, said flap being shiftable between an open position exposing said site and a closed position covering said site by said cover strip second portion.

31. The structure claimed in claim 28 wherein said dressing device comprises a dressing for a wound, incision and the like, said base strip having an aperture therein at the longitudinal center thereof, said aperture comprising said access means to said site, said site comprising said wound, incision and the like, said second portion of said cover strip being shiftable between an open position exposing said aperture and said site and a closed position covering said aperture and said site.

* * * * *